United States Patent
Bolea et al.

(10) Patent No.: US 7,205,411 B2
(45) Date of Patent: Apr. 17, 2007

(54) AMINOPYRIDINE DERIVATIVES AS MGLUR5 ANTAGONISTS

(75) Inventors: Christelle Bolea, Carouge (CH); Vincent Mutel, Pringy (FR); Jean-Philippe Rocher, Vetraz-Monthoux (FR); Anne-Sophie Bessis, Ferney-Voltaire (FR); Emmanuel Le Poul, Cessy (FR)

(73) Assignee: Addex Pharmaceuticals SA, Geneva (CH)

( * ) Notice: Subject to any disclaimer, the term of this patent is extended or adjusted under 35 U.S.C. 154(b) by 39 days.

(21) Appl. No.: 11/225,490

(22) Filed: Sep. 2, 2005

(65) Prior Publication Data

US 2006/0030601 A1 Feb. 9, 2006

Related U.S. Application Data

(63) Continuation of application No. PCT/IB04/00745, filed on Mar. 4, 2004.

(30) Foreign Application Priority Data

Mar. 4, 2003 (GB) ................... 0304901.2
Jul. 14, 2003 (GB) ................... 0316430.8

(51) Int. Cl.
*C07D 401/00* (2006.01)
*C07D 21/72* (2006.01)
*A61K 31/44* (2006.01)

(52) U.S. Cl. ............ 546/256; 546/304; 546/312; 514/333; 514/357

(58) Field of Classification Search ............ 546/256, 546/304, 312; 514/333, 357
See application file for complete search history.

(56) References Cited

U.S. PATENT DOCUMENTS 6,187,777 B1  2/2001  Norman et al.

FOREIGN PATENT DOCUMENTS

WO  WO-99/02497  1/1999

OTHER PUBLICATIONS

Jeong et. al., "Assembly and Binding Properties of Osmate Ester-Bridged Binuclear Macrocycles", J. Org. Chem. 1999, 64, 9459-9466.*

* cited by examiner

*Primary Examiner*—Thomas McKenzie
*Assistant Examiner*—Binta Robinson
(74) *Attorney, Agent, or Firm*—Peter F. Corless; Edwards Angell Palmer & Dodge LLP

(57) ABSTRACT

The invention relates to novel aminopyridine derivatives of formula (I) wherein R1 is methyl an $R_4$ and amino group —$NR_6R_7$ and $R_5$ forms an arylalkynyl- or heteroarylalkynyl-group. The compounds are useful in the prevention or treatment of central nervous system disorders as well as other disorders modulated by mGluR5 receptors

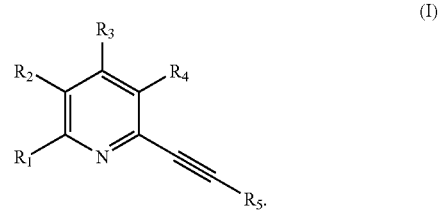

(I)

5 Claims, No Drawings

AMINOPYRIDINE DERIVATIVES AS MGLUR5 ANTAGONISTS

The present application is a continuing application of International Application PCT/IB2004/000745 having an international filing date of 4 Mar. 2004, which is incorporated by reference herein in its entirety.

Extensive literature exists relating to pyridine compounds however there is very little data concerning 3-amino-2-arylalkynyl-, 3-amino-2-heteroarylalkynyl-pyridine derivatives which are agents of the invention. The present invention relates to substituted 3-amino arylalkynyl-pyridines and 3-amino heteroarylalkynyl-pyridines.

U.S. Pat. No. 6,384,235B2 and Rodriguez et al. Angewandte Chemie, International Edition 2000, 39, 14, 2488–2490 describes 3-amino-(2-phenylethynyl)pyridine as synthetic intermediates. WO 99/40091 discloses certain 3-amino-(2-phenylethynyl) pyridines as synthetic intermediates which are subsequently ring closed.

WO 99/02497 describes certain 2-heteroalkynyl pyridines as modulating mGluRs and a very broad generic disclosure. However, none of the specifically disclosed compounds are 3-amino-2-aryl or heteroaryl ethynyl pyridines. WO 02/46166 describes various compounds having the structure phenyl-A-B as mGluR antagonists but it has no disclosure of phenyl ethynylpyridines. The already known structure in the field of mGluR5 ligands like 2-methyl-6-(phenylethynyl)-pyridine (MPEP) suffer from poor bioavailability and selectivity (R. Kuhn et al. Amino Acids, 2002, 23, 207–211; N. D. P. Cosford et al. J. Med. Chem. 2003, 46, 204–206).

U.S. Pat. No. 6,187,777 describes the compound 3-amino-4-chloro-6-methyl-2-(2-phenylethynyl)pyridine as a synthetic intermediate for compounds to modulate feeding behaviour.

It has now surprisingly been found that amino pyridine compounds of the invention show potent activity and selectivity on mGluR5 receptor and demonstrate advantageous properties over compounds of the prior art. Improvements have been observed in one or more of the following characteristics of the compounds of the invention: the selectivity for the target, the solubility, the bioavailability, the brain penetration, the activity in behavioural models of psychiatric and neurological disorders. They can be used in the treatment or prevention of mGluR5 mediated disorders.

L-glutamate is the main excitatory neurotransmitter in the mammalian brain and acts through two heterogeneous families of receptors: ionotropic and metabotropic glutamate receptors (mGluR) (Nakanishi S et al. 1998, Brain Res Brain Res Rev., 26:230–235). To date eight subtypes of mGluR have been cloned and classified into three groups on the basis of sequence similarities and pharmacological properties.

mGluR1 and mGluR5 belong to group I and initiate cellular responses through a G-protein mediated mechanism and are coupled to phospholipase C and stimulate phosphoinositide hydrolysis (Schoepp DD et al. 1999, Neuropharmacology, 38:1431–1476).

The mGluR5 receptor protein has been localized peripherally in structures involved in nociceptive transmission and recent findings suggest that mGluR5 antagonists can be used for the treatment of inflammatory and neuropathic pain, chronic and acute pain (B. A. Chizh in Amino Acids 2002, 23,169–176).

mGluR5 receptors are also abundant in CNS throughout cortex, hippocampus, caudate-putamen and nucleus accumbens. As these brain areas are thought to be involved in emotional and motivational processes, the mGluR5 receptor has been considered a potential drug target for treatment of psychiatric and neurological disorders. Treatable diseases are psychosis, epilepsy, schizophrenia, Alzheimer's disease, cognitive disorders, memory deficits, Parkinson's disease, hypoxia, ischemia, dementia caused by AIDS, migraine, depression, mood disorders and anxiety disorders. Other treatable indications are nicotine, cocaine, amphetamine, benzodiazepine, opiate or alcohol abuse or addiction and substance tolerance or dependence, bulimia nervosa, anorexia nervosa, gambling dependence, smoking, sex dependence or obsessive compulsive disorders (Brauner-Osborne H et al., 2000, J Med. Chem. 43:2609–45; Bordi F and Ugolini A. 1999, Prog Neurobiol. 59:55–79; Spooren W et al. 2003, Behav Pharmacol: 14:257–77).

The present invention relates to a method of treating or preventing a condition in a mammal, including a human, the treatment or prevention of which is affected or facilitated by the neuromodulatory effect of mGluR5 antagonists.

The present invention is concerned with novel aminopyridine derivatives, and their uses, which conform to the general formula

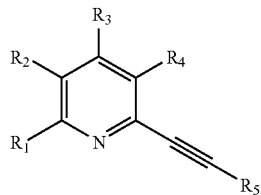

I wherein $R_1$ is methyl $R_2$ and $R_3$ are independently selected from hydrogen, halogen, nitro, $C_1$–$C_6$-alkyl;

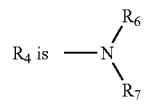

$R_6$ and $R_7$ which may be the same or different are hydrogen or a group of formula:

—X—$R_8$ wherein X is =CH—N($R_8$)$_2$ and $R_8$ is hydrogen, $C_1$–$C_6$-alkyl, halo-$C_1$–$C_6$-alkyl, aryl, aryl-$C_1$–$C_6$-alkyl, heteroaryl or heteroaryl-$C_1$–$C_6$-alkyl;

$R_5$ represents a group of formula

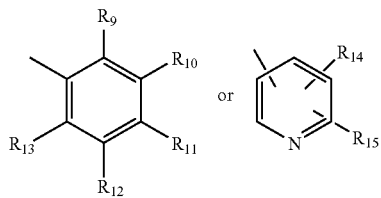

wherein

R$_9$, R$_{10}$, R$_{11}$, R$_{12}$ and R$_{13}$ independently are hydrogen, halogen, cyano, nitro, C$_1$–C$_6$-alkyl, halo-C$_1$–C$_6$-alkyl, C$_1$–C$_6$-alkoxy, carboxy-C$_1$–C$_6$-alkyl or carboxyaryl;

R$_{14}$ and R$_{15}$ independently are as defined for R$_9$–R$_{13}$ above;

or pharmaceutically acceptable salts, hydrates or solvates of such compounds for the prevention or treatment of central nervous system (CNS) disorders as well as other disorders modulated by mGluR5 receptors.

The compound 3-amino-4-chloro-6-methyl-2-(2-phenyl-ethynyl)pyridine as such is disclaimed from the invention.

In the above definition, the term "C$_1$–C$_6$-alkyl" includes groups such as methyl, ethyl, propyl, isopropyl, butyl, isobutyl, sec-butyl, tert-butyl, pentyl, isopentyl, neopentyl, tert-pentyl, hexyl or the like. "Hydroxy-C$_1$–C$_6$-alkyl" includes groups such as hydroxymethyl, 2-hydroxyethyl, 3-hydroxypropyl, 4-hydroxybutyl, 5-hydroxypentyl, 6-hydroxyhexyl and the like. "C$_1$–C$_6$-alkoxy" includes groups such as methoxy, ethoxy, propoxy, isopropoxy, butoxy, isobutoxy, tert-butoxy, pentyloxy, hexyloxy or the like.

"Halogen" includes atoms such as fluorine, chlorine and iodine. "Halo-C$_1$–C$_6$-alkyl" includes groups such as chloromethyl, dichloromethyl, trichloromethyl, fluoromethyl, difluoromethyl, trifluoromethyl, bromomethyl, 1-chloroethyl, 1,1-dichloroethyl, 2-chloroethyl, 2,2,2-trichloroethyl, 1-fluoroethyl, 1,1-difluoroethyl, 2-fluoroethyl, 2,2,2-trifluoroethyl, 2-bromoethyl, 3-chloropropyl, 3-fluoropropyl, 3-bromopropyl and the like. "Halo-C$_1$–C$_6$-alkoxy" includes groups such as chloromethoxy, fluoromethoxy, difluoromethoxy, trifluoromethoxy, 2-fluoroethoxy, 2,2,2-trifluoroethoxy and the like.

"Carboxy-C$_1$–C$_6$-alkyl" includes groups such as carboxymethyl, 2-carboxyethyl, 3-carboxypropyl, 4-carboxybutyl, 5-carboxypentyl, 6-carboxyhexyl or the like.

"Aryl" includes C$_6$–C$_{10}$ aryl groups such as phenyl, 1-naphtyl, 2-naphtyl and the like.

"Heteroaryl" includes 5–10 membered heterocyclic groups containing 1 to 4 heteroatoms selected from oxygen, nitrogen or sulphur to form a ring such as furyl (furan ring), benzofuranyl (benzofuran), thienyl (thiophene), benzothiophenyl (benzothiophene), pyrrolyl (pyrrole ring), imidazolyl (imidazole ring), pyrazolyl (pyrazole ring), thiazolyl (thiazole ring), isothiazolyl (isothiazole ring), triazolyl (triazole ring), tetrazolyl (tetrazole ring), pyridil (pyridine ring), pyrazynyl (pyrazine ring), pyrimidinyl (pyrimidine ring), pyridazinyl (pyridazine ring), indolyl (indole ring), isoindolyl (isoindole ring), benzoimidazolyl (benzimidazole ring), purinyl group (purine ring), quinolyl (quinoline ring), phtalazinyl (phtalazine ring), naphtyridinyl (naphtyridine ring), quinoxalinyl (quinoxaline ring), cinnolyl (cinnoline ring), pteridinyl (pteridine ring), oxazolyl (oxazole ring), isoxazolyl (isoxazole ring), benzoxazolyl (benzoxazole ring), furazanyl (furazan ring) and the like.

"Heteroaryl-C$_6$–C$_{10}$-alkyl" includes groups wherein examples of heteroaryl are the same as those illustrated in the above definition, such as 2-furylmethyl, 3-furylmethyl, 2-thienylmethyl, 3-thienylmethyl, 2-imidazolylmethyl, 2-thiazolylmethyl, 2-pyridylmethyl, 3-pyridylmethyl, 4-pyridylmethyl, 2-quinolylmethyl and the like.

Preferred compounds of the present invention are compounds of formula I-A depicted below

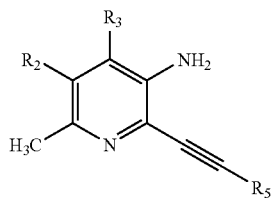

I-A wherein

R$_2$ and R$_3$ are independently selected from hydrogen, C$_1$–C$_6$-alkyl;

R$_5$ represents a group of formula

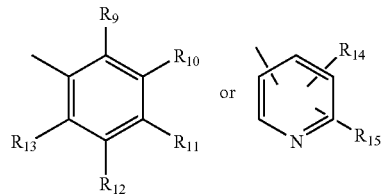

wherein

R$_9$, R$_{10}$, R$_{11}$, R$_{12}$ and R$_{13}$ independently are hydrogen, halogen, cyano, nitro, C$_1$–C$_6$-alkyl, halo-C$_1$–C$_6$-alkyl, C$_1$–C$_6$-alkoxy, carboxy-C$_1$–C$_6$-alkyl or carboxyaryl;

R$_{14}$ and R$_{15}$ independently are as defined for R$_9$–R$_{13}$ above;

or pharmaceutically acceptable salts, hydrates or solvates of such compounds.

More preferred compounds of the present invention are compounds of formula I-B

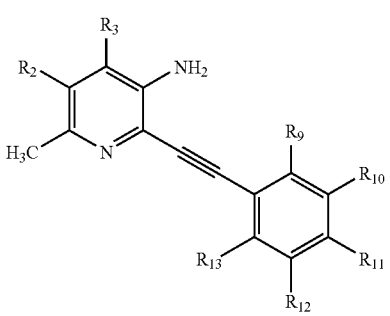

I-B wherein

R$_2$ and R$_3$ are independently selected from hydrogen, C$_1$–C$_6$-alkyl;

R$_9$, R$_{10}$, R$_{11}$, R$_{12}$ and R$_{13}$ independently are hydrogen, halogen, cyano, nitro, C$_1$–C$_6$-alkyl, halo-C$_1$–C$_6$-alkyl, C$_1$–C$_6$-alkoxy, carboxy-C$_1$–C$_6$alkyl or carboxyaryl;

or pharmaceutically acceptable salts, hydrates or solvates of such compounds.

Particularly preferred compounds of the present invention are compounds of formula I-C

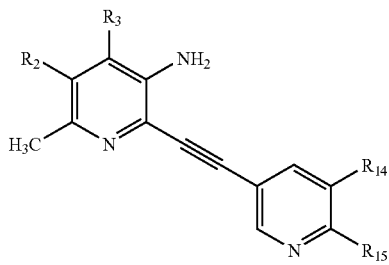

wherein
$R_2$ and $R_3$ are independently selected from hydrogen, $C_1$–$C_6$-alkyl;
$R_{14}$ and $R_{15}$ independently are hydrogen, halogen, cyano, nitro, $C_1$–$C_6$-alkyl, halo-$C_1$–$C_6$-alkyl, $C_1$–$C_6$-alkoxy, carboxy-$C_1$–$C_6$-alkyl or carboxyaryl;

or pharmaceutically acceptable salts, hydrates or solvates of such compounds.

Specifically preferred compounds are:
(6-Methyl-2-phenylethynyl-pyridin-3-yl)amine
N,N-Dimethyl-N'-(6-methyl-2-phenylethynyl-pyridin-3-yl)-formamidine
(2-(3-Fluoro-phenylethynyl)-6-methyl-pyridin-3-yl)amine
(2-(3-Methoxy-phenylethynyl)-6-methyl-pyridin-3-yl)amine
(6-Methyl-2-pyridin-3-ylethynyl-pyridin-3-yl)amine
(2-(4-Fluoro-phenylethynyl)-6-methyl-pyridin-3-yl)amine
(2-(3,5-Difluoro-phenylethynyl)-6-methyl-pyridin-3-yl)amine
(2-(5-Fluoro-pyridin-3-ylethynyl)-6-methyl-pyridin-3-yl)amine
3-(3-Amino-6-methyl-pyridin-2-ylethynyl)-benzonitrile
(2-(5-Chloro-pyridin-3-ylethynyl)-6-methyl-pyridin-3-yl)amine
(2-(3-Chloro-phenylethynyl)-6-methyl-pyridin-3-yl)amine
(2-(3-Fluoro-phenylethynyl)-4,6-dimethyl-pyridin-3-yl)amine
(2-(3-Chloro-phenylethynyl)4,6-dimethyl-pyridin-3-yl)amine The present invention relates to the pharmaceutically acceptable acid addition salts of compounds of the formula (I) or compositions comprising compounds of formula (I) together with pharmaceutically acceptable carriers or excipients.

The present invention relates to a method of treating or preventing a condition in a mammal, including a human, the treatment or prevention of which is affected or facilitated by the neuromodulatory effect of mGluR5 antagonists.

The present invention relates to a method useful for treating or preventing peripheral and central nervous system disorders selected from: substance tolerance or dependence, anxiety disorders, depression, mood disorders, psychiatric disease such as psychosis, inflammatory or neuropathic pain, memory deficits, Alzheimer's disease, Parkinson's disease, migraine, ischemia, drug abuse and addiction.

The present invention relates to pharmaceutical compositions which provide from about 0.01 to 1000 mg of the active ingredient per unit dose. The compositions may be administered by any suitable route. For example orally in the form of capsules, etc., parenterally in the form of solutions for injection, topically in the form of unguents or lotions, ocularly in the form of eye-drops, rectally in the form of suppositories, intranasally or transcutaneously in the form of delivery system like patches.

The pharmaceutical formulations of the invention may be prepared by conventional methods in the art; the nature of the pharmaceutical composition employed will depend on the desired route of administration. The total daily dose usually ranges from about 0.05–2000 mg.

The invention also provides for use of compounds or compositions as defined above in the manufacture of medicaments for treatment or prevention of the stated disorders.

The compounds of Formula I may be prepared by general routes of synthesis as disclosed in the following methods.

Scheme 1 illustrates the preparation of compounds of formula I by reacting an alkyne derivative, for example ethynylbenzene, with a substituted aminopyridine (or a precursor), for example 2-bromo-6-methyl-pyridin-3-ylamine. Thus in Scheme 1, $R_1$, $R_2$, $R_3$, $R_5$, $R_6$ and $R_7$ are as defined above and Q includes halides such as Cl, Br, I or trifluoromethanesulfonyl and paratoluenesulfonyl. This general route of synthesis has been described in M. H. Norman et al. J. Med. Chem. 2000, 43, 4288–4312.

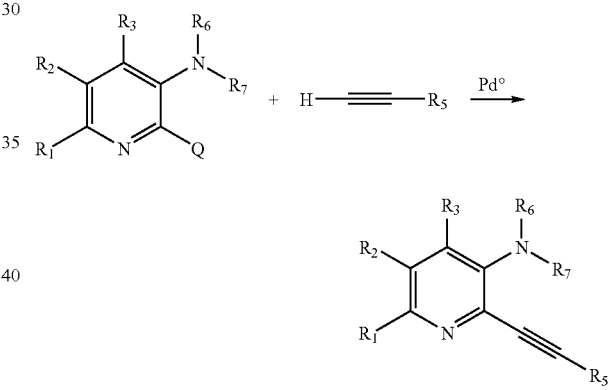

This palladium catalyzed C—C coupling reaction requires a catalyst such as $PdCl_2(PPh_3)_2$, $Pd(PPh_3)_4$, $Pd(OAc)_2$ or Pd on carbon in a suitable solvent like DMF, acetonitrile or benzene. Typically a co-catalyst such as copper(I) iodide and a base (e.g., triethylamine, diisopropylamine, KOAc . . . ) will also be present in the reaction mixture. The coupling reaction typically proceeds by allowing the reaction temperature to warm slowly from about 0° up to ambient temperature, or heated to a temperature anywhere between 30° C. and 150° C. The reaction mixture is then maintained at a suitable temperature for a time in the range of about 1 up to 24 hours, with about 12 hours typically being sufficient. The product from the reaction can be isolated and purified employing standard techniques, such as solvent extraction, chromatography, crystallization, distillation, sublimation, and the like.

In another embodiment of the present invention, depicted in Scheme 2, an alkynyl-substituted aminopyridine (or a precursor) is reacted with a compound bearing a reactive functional group Q as defined above.

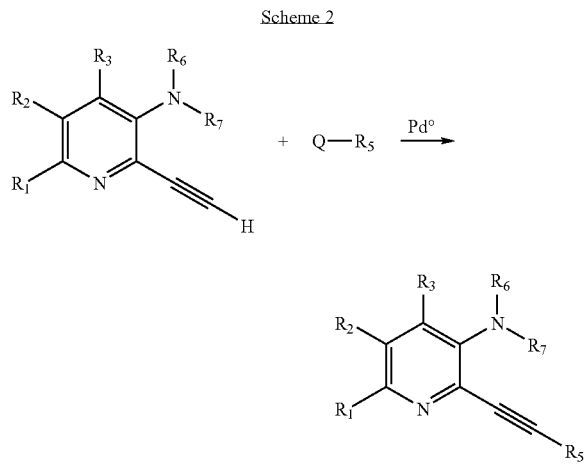

Thus, in Scheme 2, $R_1$, $R_2$, $R_3$, $R_5$, $R_6$, $R_7$, Q, the catalysts and reaction conditions are as described for Scheme 1.

Another embodiment of the present invention is illustrated in Scheme 3. A substituted aminopyridine (or a precursor) is reacted with an alkene derivative, as described in C. Niu et al. Tetrahedron, 1998, 54, 6311–6318, in a manner similar to the procedure presented for Scheme 1.

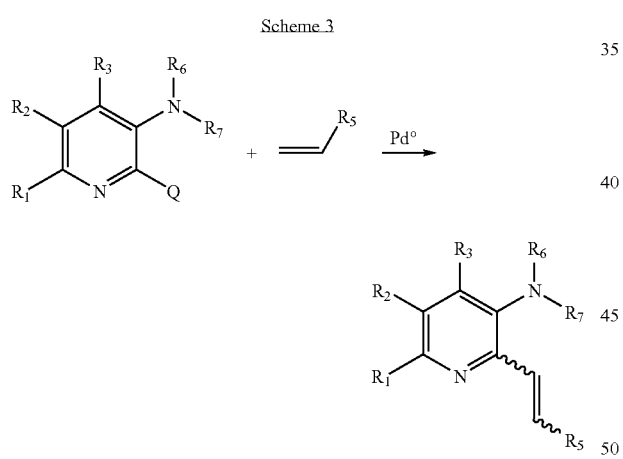

The alkene derivative product from Scheme 3 may be converted to an alkyne derivative using the approach outlined in Scheme 4.

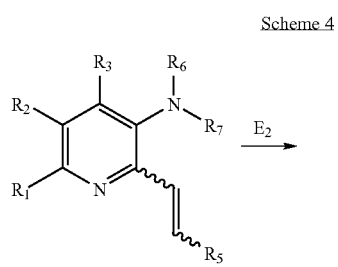

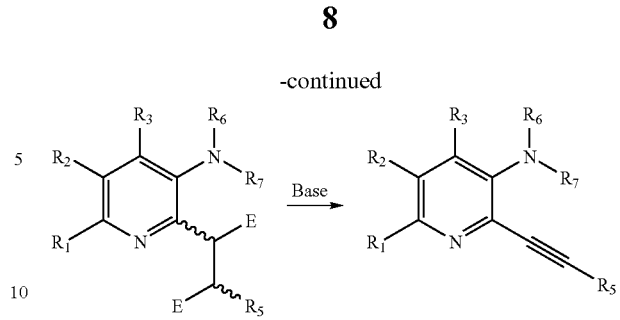

This synthetic route refers to the methods described in G. R. Newkome et al. J. Org. Chem. 1980, 45, 4380–4385 or F. Gasparini et al. Bioorg. Med. Chem. Lett. 2002, 12, 407–410. The alkene derivatives may be treated with a halogenating agent such as chlorine or bromine in $CHCl_3$ or $CCl_4$. The resulting halogenated derivatives are then treated with a suitable base such as NaOH, KOH or KO$^t$Bu, which promotes a double elimination reaction to afford the alkyne. The reaction is carried out in a solvent like ethanol, tert-butanol, THF, etc. at an appropriate temperature, usually between 0° C. and 150° C.

In another embodiment of the present invention, a substituted aminopyridine (or a precursor) is reacted with an aldehyde to provide a substituted alkene following the procedure developed in D. Guay et al. Bioorg. Med. Chem. Lett. 1998, 8, 453–458. (Scheme 5)

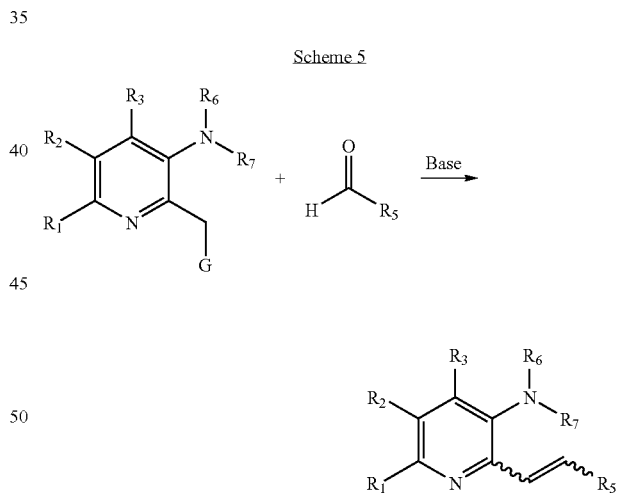

Thus, in Scheme 5, G is $PR_3$ or $P(O)(OR)_2$. The reaction is carried out with suitable catalysts including bases such as KH, NaH, n-butyllithium etc., in THF, acetonitrile, benzene, etc., at an appropriate temperature, usually between about 0° C. and 150° C.

In yet another embodiment of the present invention, a substituted heterocyclic aldehyde is reacted with a compound containing an activated methylene to provide a substituted alkene following the procedure developed in M. Cushman et al. J. Med. Chem. 1991, 34, 2579–2588. (Scheme 6)

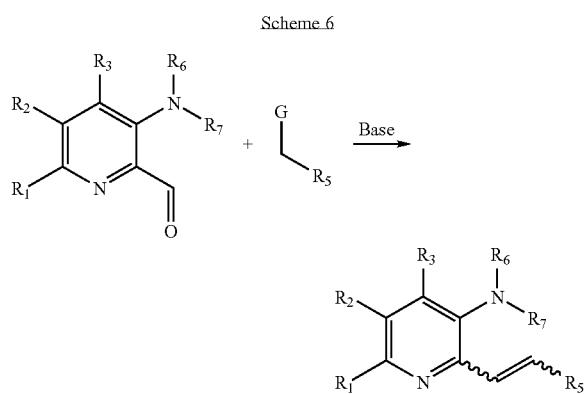

Scheme 6

Thus, in Scheme 6, G, the catalysts and reaction conditions are as described for Scheme 5.

The alkene products from the reactions in Scheme 5 and Scheme 6 may be converted to an alkyne derivative using reagents and conditions as described for Scheme 4.

Substituted aminopyridines of formula I-A can be obtained from the corresponding nitropyridine compounds by a selective reduction of the nitro moiety with the method described in S. Glase et al. J. Med. Chem. 1996, 39, 3179–3187, using a mixture of Fe and aqueous HCl as the reducing agent.

The reactions described in scheme 1 to 6 can lead to free amino compounds when $R_6$ and $R_7$ are hydrogen. A subsequent functionalisation into amidine compounds of the invention can be performed according to standard methods familiar to those skilled in the art of converting free amino derivatives.

The compounds of Formula I which are basic in nature can form a wide variety of different pharmaceutically acceptable salts with various inorganic and organic acids. These salts are readily prepared by treating the base compounds with a substantially equivalent amount of the chosen mineral or organic acid in a suitable organic solvent such as methanol, ethanol or isopropanol.

Pharmacology

Some of the compounds of Formula I have been tested according to the following methods.

mGluR5 Binding Assay

Affinity of compounds of the invention was examined following a radioligand binding technique using whole rat brain and tritiated 2-methyl-6-(phenylethynyl)-pyridine ([$^3$H]-MPEP) as a ligand following similar methods to those described in F. Gasparini et al. Bioorg. Med. Chem. Lett. 2002, 12, 407–409 and in J. F. Anderson et al. J. Pharmacol. Exp. Ther. 2002, 303, 3,1044–1051.

Membrane Preparation:

Cortices were dissected out from brains of 200–300 g Sprague-Dawley rats (Charles River Laboratories, L'Arbresle, France). Tissues were homogenized in 10 volumes (vol/wt) of ice-cold 50 mM Hepes-NaOH (pH 7.4) using a Polytron disrupter (Kinematica AG, Luzern, Switzerland) and centrifuged for 30 min at 40,000 g. (4° C.). The supernatant was discarded and the pellet washed twice by resuspension in 10 volumes 50 mM HEPES-NaOH. Membranes were then collected by centrifugation and washed before final resuspension in 10 volumes of 20 mM HEPES-NaOH, pH 7.4. Protein concentration was determined by the Bradford method (Bio-Rad protein assay, Reinach, Switzerland) with bovine serum albumin as standard.

[$^3$H]-MPEP Binding Experiments:

Membranes were thawed and resuspended in binding buffer containing 20 mM HEPES-NaOH, 3 mM $MgCl_2$, 100 mM NaCl, pH 7.4. Competition studies were carried out by incubating for 1 h at 4° C.: 3 nM [$^3$H]-MPEP (46,85 Ci/mmol, Tocris, Cookson Ltd, Bristol, U.K.), 50 μg membrane and a concentration range of 0.03 nM–30 μM of compounds, for a total reaction volume of 300 μl. The non-specific binding was defined using 30 μM MPEP. Reaction was terminated by rapid filtration over glass-fiber filter plates (Unifilter 96-well GF/B filter plates, Perkin-Elmer, Schwerzenbach, Switzerland) using 4×400 μl ice cold buffer using cell harvester (Filtermate, Perkin-Elmer, Downers Grove, USA). Radioactivity was determined by liquid scintillation spectrometry using a 96-well plate reader (TopCount, Perkin-Elmer, Downers Grove, USA).

Data Analysis:

The inhibition curves were generated using the Prism GraphPad program (Graph Pad Software Inc, San Diego, USA). IC50 determinations were made from data obtained from 8 point concentrations response curves using a nonlinear regression analysis.

The compounds of this application as measured in the assay described above have IC50 values in the range of less than 10 μM. Preferred compounds include the examples n° 3, 7, 10, 12 and 13 which have IC50 values of less than 30 nM.

In-Vitro Selectivity Profile

Compounds of the invention show an improved selectivity on mGluR5 receptor.

This indicates a greater specificity and a better safety profile.

In-Vivo

Compounds of the invention are effective in models demonstrating the usefulness of the compounds for treating neuropathic inflammatory pain (B. A. Chizh, Amino Acids 2002, 23, 169–176), anxiety (W. P. J. M. Spooren et al. J. Pharmacol. Exp. Ther. 2000, 295, 3, 1267–1275; W. P. J. M. Spooren et al. Eur. J. Pharmacol. 2002, 435, 161–170), Parkinson disease (N. Breysse et al. J. Neurosci. 2003, 10, 23, 23, 8302–8309), migraine (P. De Vries et al. 1999, 375, 61–74), depression (I. A. Paul and P. Skolnick, Ann. N Y Acad. Sci. 2003, 1003, 250–72) and addictive disorders (N. E. Paterson et al. Psychopharmacology 2003, 167, 257–264; C. Chiamulera et al. Nature Neurosci. 2001, 4, 9, 873–874).

The compounds of the present invention present a high selectivity and affinity for mGluR5 receptor. As functional antagonists, they are useful for the production of medications, especially for the treatment or prevention of central nervous system disorders as well as other disorders modulated by this receptor.

Reasonable variations are not to be regarded as a departure from the scope of the invention. It will be obvious that the thus described invention may be varied in many ways by those skilled in the art.

The following non-limiting examples are intending to illustrate the invention. The physical data given for the compounds exemplified are consistent with the assigned structure of those compounds.

EXAMPLES

Unless otherwise noted, all starting materials were obtained from commercial suppliers and used without fur-

| | |
|---|---|
| ¹H (proton) | ml (milliliters) |
| CHCl₃ (chloroform) | μl (microliters) |
| CuI (copper iodide) | μmol (micromoles) |
| DCM (dichloromethane) | mmol (millimoles) |
| dec. (decomposition) | M.p. (melting point) |
| DMSO[D₆] (deuterated dimethylsulfoxyde) | NH₄OH (ammonium hydroxide) |
| h (hour) | NaOH (sodium hydroxide) |
| LC-MS (Liquid Chromatography Mass Spectrometry) | Na₂SO₄ (sodium sulphate) |
| M (molar) | NMR (Nuclear Magnetic Resonance) |
| MeOH (methanol) | PBr₃ (Phosphorus tribromide) |
| mg (milligrams) | PdCl₂(PPh₃)₂ (Bis(triphenylphosphine) palladium (II) dichloride |
| MHz (megahertz) | RT (Retention Time) |

All reactions are conducted under an inert atmosphere at room temperature unless otherwise noted.

$^1$H NMR spectra were recorded either on a Bruker ARX400 or on a Bruker 500 MHz. Chemical shifts are expressed in parts per million (ppm, δ units). Coupling constants are in units of hertz (Hz) Splitting patterns describe apparent multiplicities and are designated as s (singulet), d (doublet), t (triplet), q (quartet) and m (multiplet).

LC-MS spectra were recorded on a Waters Micromass ZQ 2996 system by the following conditions: Column 3.0*50 mm stainless steel packed with 5 μm XTerra RP C-18; flow rate 0.8 ml/min; mobile phase: A phase=0.07% formic acid in water, B phase=0.07% formic acid in acetonitrile. 0–0.5 min (A: 95%, B: 5%), 0.5–6.0 min (A: 0%, B: 100%), 6.0–6.5 min (A: 95%, B: 5%), 6.5–7 min (A: 95%, B: 5%); UV detection Diode Array: 200–400 nm; Injection volume: 5 μl. All mass spectra were taken under electrospray ionisation (ESI) methods.

Melting point determination was performed on a Buchi B-540 apparatus.

The reactions were monitored by thin-layer chromatography on 0.20 mm silica gel plates (60F$_{254}$, Merck or G/UV$_{254}$ Macherey Nagel) and visualized with UV light. Flash column chromatography was performed on silica gel (220–440 mesh, Fluka).

Example 1

(6-Methyl-2-phenylethynyl-pyridin-3-yl)amine hydrochloride

To a solution of CuI (10 mg, 50 μmol) in triethylamine (5 ml) were added (2-bromo-6-methyl-pyridin-3-yl)amine (200 mg, 1.07 mmol) and (PPh₃)₂PdCl₂ (36 mg, 50 μmol). The reaction mixture was cooled to 0° C. and phenylacetylene (176 μl, 1.60 mmol) was added. The reaction mixture was allowed to warm to room temperature and then heated under reflux for 14 h. The solvent was evaporated and the crude residue was purified by flash chromatography (hexane/ethyl acetate 4:1) to yield 105 mg (0.50 mmol, 47%) of (6-methyl-2-phenylethynyl-pyridin-3-yl)amine as a yellow solid.

R$_f$: 0.09 (Hexane/ethyl acetate 4:1). M. p.: 154–155° C. $^1$H NMR (CDCl₃, 400 MHz) δ: 2.47 (s, 3 H), 4.13–4.17 (br. s, 2 H), 6.93–7.01 (2 H), 7.34–7.39 (3 H), 7.57–7.63 (2 H). (6-methyl-2-phenylethynyl-pyridin-3-yl)amine (105 mg, 0.50 mmol) was dissolved in CHCl₃ (2 ml) and treated with 1.56 ml (1.25 mmol) of 0.8 M hydrochloric acid solution in diethyl ether. After evaporation of the solvent and trituration of the residue with ethyl acetate, 107 mg (0.44 mmol, 87%) of the title hydrochloride were obtained as a yellowish solid.

R$_f$: 0.50 (Hexane/ethyl acetate 1:1). M. p.: 183° C. $^1$H NMR (DMSO[D₆], 400 MHz) δ: 2.57 (s, 3 H), 3.20–4.00 (br. s, 3 H), 7.51–7.57 (4 H), 7.71 (d, J=8.8 Hz, 1 H), 7.80–7.84 (2 H). LC-MS (RT): 2.14 min.; MS (ES+) gave m/z: 209.1.

Example 2

N,N-Dimethyl-N'-(6-methyl-2-phenylethynyl-pyridin-3-yl)-formamidine

A solution of N,N-dimethylformamidedimethylacetal (80 μl, 0.60 mmol) and (6-methyl-2-phenylethynyl-pyridin-3-yl)amine (102 mg, 0.49 mmol) from Example 1, in toluene (1 ml) was heated for 20 h, at 80° C. The solvent was evaporated and the residue was purified by flash chromatography (hexane/ethyl acetate 4:1) to give 24 mg (0.09 mmol, 15%) of N,N-dimethyl-N'-(6-methyl-2-phenylethynyl-pyridin-3-yl)-formamidine as a yellow oil.

R$_f$: 0.17 (Hexane/ethyl acetate 4:1). $^1$H NMR (DMSO[D₆], 400 MHz) δ: 2.42 (s, 3 H), 3.05 (s, 3 H), 3.07 (s, 3 H), 7.14 (d, J=8.8 Hz, 1 H), 7.32 (d, J=8.8 Hz, 1 H), 7.44–7.58 (4 H), 7.87 (s, 1 H), 7.93 (d, J=7.2 Hz, 1 H). LC-MS (RT): 0.61 min.; MS (ES+) gave m/z: 264.1.

Example 3

(2-(3-Fluoro-phenylethynyl)-6-methyl-pyridin-3-yl) amine hydrochloride

Following the same procedure as described in Example 1, (2-bromo-6-methyl-pyridin-3-yl)amine (200 mg, 1.07 mmol) reacted with (PPh₃)₂PdCl₂ (36 mg, 0.05 mmol), CuI (10 mg, 0.05 mmol) and 1-ethynyl-3-fluorobenzene (148 μl, 1.28 mmol) in triethylamine (5 ml). The crude residue was purified by flash chromatography (hexane/ethyl acetate 4:1) to yield 145 mg (0.64 mmol, 60%) of (2-(3-fluoro-phenylethynyl)-6-methyl-pyridin-3-yl)amine as a pale yellow solid. The hydrochloride of (2-(3-fluoro-phenylethynyl)-6-methyl-pyridin-3-yl)amine was prepared as described in Example 1 to yield 148 mg (0.56 mmol, 88%) of the title hydrochloride as a yellow solid.

R$_f$: 0.52 (Hexane/ethyl acetate 1:1). M. p.: 199–200° C. (dec.). $^1$H NMR (DMSO[D₆], 400 MHz) δ: 2.52 (s, 3 H), 6.20–7.24 (br. s, 2 H), 7.35–7.43 (m, 1 H), 7.48 (d, J=8.0 Hz, 1 H), 7.52–7.61 (2 H), 7.62–7.67 (m, 1 H), 7.68–7.72 (m, 1 H). LC-MS (RT): 2.26 min.; MS (ES+) gave m/z: 227.1. Anal. Calcd for C₁₄H₁₂ClFN₂: C, 64.01%; H, 4.60%; Cl, 13.50%; F, 7.23%; N, 10.66%. Found: C, 63.30%; H, 4.62%; Cl, 13.56%; F, 6.98%; N, 10.57%.

Example 4

(2-(3-Methoxy-phenylethynyl)-6-methyl-pyridin-3-yl)amine

Following the same procedure as described in Example 1, (2-bromo-6-methyl-pyridin-3-yl)amine (200 mg, 1.07 mmol) reacted with (PPh₃)₂PdCl₂ (37 mg, 0.05 mmol), CuI (10 mg, 0.05 mmol) and 1-ethynyl-3-methoxy-benzene (204 μl, 1.60 mmol) in triethylamine (5 ml) during 1.5 h. The crude residue was purified by flash chromatography (hexane/ethyl acetate 4:1) to yield 118 mg (0.50 mmol, 46%) of (2-(3-methoxy-phenylethynyl)-6-methyl-pyridin-3-yl)amine as a yellow brown solid.

$R_f$: 0.30 (Hexane/ethyl acetate 1:1). M. p.: 165–166° C. $^1$H NMR (DMSO[D$_6$], 400 MHz) δ: 2.60 (s, 3 H), 3.85 (s, 3 H), 7.11–7.16 (m, 1 H), 7.37–7.49 (3 H), 7.56 (d, J=8.4 Hz, 1 H), 7.77 (d, J=8.8 Hz, 1 H). LC-MS (RT): 2.31 min.; MS (ES+) gave m/z: 239.1.

Example 5

(6-Methyl-2-pyridin-3-ylethynyl-Pyridin-3-yl)amine hydrochloride

Following the same procedure as described in Example 1, (2-bromo-6-methyl-pyridin-3-yl)amine (200 mg, 1.07 mmol) reacted with (PPh$_3$)$_2$PdCl$_2$ (37 mg, 0.05 mmol), CuI (10 mg, 0.05 mmol) and 3-ethynyl-pyridine (110 mg, 1.07 mmol) in triethylamine (1.6 ml). The crude residue was purified by flash chromatography (DCM-DCM/MeOH 97:3) to yield 100 mg (0.48 mmol, 49%) of (6-methyl-2-pyridin-3-ylethynyl-pyridin-3-yl)amine as a yellow powder. The hydrochloride of (6-methyl-2-pyridin-3-ylethynyl-pyridin-3-yl)amine was prepared as described in Example 1 to yield after trituration with pentane 145 mg (100%) of the title hydrochloride as a yellow solid.

M. p.: 156.4–158° C. $^1$H NMR (DMSO[D$_6$], 500 MHz) δ: 2.54 (s, 3 H), 7.52 (d, J=9 Hz, 1 H), 7.61–7.68 (m, 1 H), 7.69 (d, J=9.0, 1 H), 8.25 (d, J=7.5, 1 H), 8.68–8.86 (br. s, 1 H), 8.93–9.15 (br. s, 1 H). LC-MS (RT): 0.65 min.; MS (ES+) gave m/z: 210.1.

Example 6

(2-(4-Fluoro-phenylethynyl)-6-methyl-pyridin-3-yl)amine hydrochloride

Following the same procedure as described in Example 1, (2-bromo-6-methyl-pyridin-3-yl)amine (200 mg, 1.07 mmol) reacted with (PPh$_3$)$_2$PdCl$_2$ (36 mg, 0.05 mmol), CuI (10 mg, 0.05 mmol) and 1-ethynyl-4-fluorobenzene (184 μl, 1.07 mmol) in triethylamine (5 ml). The crude residue was purified by flash chromatography (hexane/ethyl acetate 7:3) to yield 164 mg (0.72 mmol, 68%) of (2-(4-fluoro-phenylethynyl)-6-methyl-pyridin-3-yl)amine as a yellow solid. The hydrochloride of (2-(4-fluoro-phenylethynyl)-6-methyl-pyridin-3-yl)amine was prepared as described in Example 1 to yield after trituration with ethyl acetate 154 mg (0.51 mmol, 71%) of the title hydrochloride as a yellow solid.

$R_f$: 0.43 (hexane/ethyl acetate 1:1). M. p.: 122° C. (dec.). $^1$H NMR (DMSO[D$_6$], 400 MHz) δ: 2.53 (s, 3 H), 4.45–5.54 (br. s, 2 H), 7.36–7.43 (2 H), 7.52 (d, J=8.8 Hz, 1 H), 7.67 (d, J=8.8 Hz, 1 H), 7.82–7.89 (2 H). LC-MS (tr): 2.24 min.; MS (ES+) gave m/z: 227.1.

Example 7

(2-(3,5-Difluoro-phenylethynyl)-6-methyl-pyridin-3-yl)amine hydrochloride

Following the same procedure as described in Example 1, (2-bromo-6-methyl-pyridin-3-yl)amine (800 mg, 4.28 mmol) reacted with (PPh$_3$)$_2$PdCl$_2$ (150 mg, 0.21 mmol), CuI (41 mg, 0.21 mmol) and ethynyltrimethylsilane (840 mg, 8.55 mmol) in triethylamine (30 ml). The crude residue was purified by flash chromatography (hexane/ethyl acetate 8:2) to yield 330 mg (1.61 mmol, 38%) of (6-methyl-2-trimethylsilanylethynyl-pyridin-3-yl)amine as a beige solid.

(6-methyl-2-trimethylsilanylethynyl-pyridin-3-yl)amine (330 mg, 1.61 mmol) was dissolved in MeOH (3 ml) and cooled to 0° C., to the resulting solution was added 1 M solution of NaOH (1.6 ml). The ice bath was removed and the reaction mixture was stirred at room temperature for 4 h. 90 μl of acetic acid was added. The reaction mixture was partially concentrated and the residue was extracted with ethyl acetate. The organic layers were washed with water, brine, dried over Na$_2$SO$_4$, filtered and concentrated to yield 160 mg (1.21 mmole, 75%) of (2-ethynyl-6-methyl-pyridin-3-yl)amine as a brown solid which was used in the next step without further purification.

To a solution of CuI (4.3 mg, 23 μmol) in triethylamine (5 ml) were added (2-ethynyl-6-methyl-pyridin-3-yl)amine (60 mg, 0.45 mmol), (PPh$_3$)$_2$PdCl$_2$ (16 mg, 23 μmol), and 1,3-difluoro-5-iodobenzene (109 mg, 0.45 mmol). The reaction mixture was stirred at room temperature for 20 h. The solvent was evaporated to afford a brown oil which was taken up in DCM and the solution was washed with water. The aqueous phase was extracted twice with DCM. The organic phases were dried over Na$_2$SO$_4$, filtered and concentrated. The crude residue was purified by flash chromatography (hexane/ethyl acetate 7:3) to yield 64 mg (0.26 mmol, 58%) of (2-(3,5-difluoro-phenylethynyl)-6-methyl-pyridin-3-yl)amine as a yellow solid.

The hydrochloride of (2-(3,5-difluoro-phenylethynyl)-6-methyl-pyridin-3-yl)amine was prepared as described in Example 1 to yield after trituration with diethyl ether 64 mg (0.20 mmol, 78%) of the title hydrochloride as a yellow powder.

$R_f$: 0.61 (hexane/ethyl acetate 1:1). M.p.: 212° C. (dec.). $^1$H NMR (DMSO[D$_6$], 400 MHz) δ: 2.49 (s, 3 H), 6.12–7.08 (br. s, 2 H), 7.44–7.55 (2 H), 7.56–7.68 (3 H).). LC-MS (RT): 2.39 min.; MS (ES+) gave m/z: 245.0.

Example 8

(2-(5-Fluoro-pyridin-3-ylethynyl)-6-methyl-pyridin-3-yl)amine hydrochloride

To a solution of CuI (11 mg, 0.06 mmol) in triethylamine (5 ml) were added (2-ethynyl-6-methyl-pyridin-3-yl)amine (40 mg, 0.30 mmol, described in Example 7), (PPh$_3$)$_2$PdCl$_2$ (21 mg, 0.06 mmol), and 3-fluoro-5-iodopyridine (111 mg, 0.45 mmol). The reaction mixture was stirred at room temperature for 14 h. The solvent was evaporated. The crude residue was purified by flash chromatography (cyclohexane/ethyl acetate 7:3) to yield 15 mg (66 μmol, 22%) of (2-(5-fluoro-pyridin-3-ylethynyl)-6-methyl-pyridin-3-yl)amine as a yellow solid.

The hydrochloride of (2-(5-fluoro-pyridin-3-ylethynyl)-6-methyl-pyridin-3-yl)amine was prepared as described in Example 1 to yield after trituration with ethyl acetate 6 mg (20 μmol, 30%) of the title hydrochloride as a brown semi-solid.

$R_f$: 0.31 (cyclohexane/ethyl acetate 7:3). LC-MS (RT): 1.71 min.; MS (ES+) gave m/z: 228.0.

Example 9

3-(3-Amino-6-methyl-pyridin-2-ylethynyl)-benzonitrile hydrochloride

To a solution of CuI (2.4 mg, 12 μmol) in triethylamine (4 ml) were added (2-ethynyl-6-methyl-pyridin-3-yl)amine (33 mg, 0.33 mmol described in Example 7), (PPh$_3$)$_2$PdCl$_2$ (8.8 mg, 12 µmol), and 3-iodobenzonitrile (57 mg, 0.25 mmol). The reaction mixture was stirred at room temperature for 48 h. The solvent was evaporated and the crude residue was purified by flash chromatography (cyclohexane/ethyl acetate 1:1) to yield 16 mg (69 µmol, 21%) of 3-(3-amino-6-methyl-pyridin-2-ylethynyl)-benzonitrile as a pale yellow solid.

The hydrochloride of 3-(3-amino-6-methyl-pyridin-2-yl-ethynyl)-benzonitrile was prepared as described in Example 1 to yield after trituration with diethyl ether 10 mg (33 µmol, 47%) of the title hydrochloride as a yellow powder.

R$_f$: 0.36 (hexane/ethyl acetate 1:1). M. p.: 132.4–134° C. LC-MS (RT): 2.13 min.; MS (ES+) gave m/z: 234.1.

Example 10

(2-(5-Chloro-pyridin-3-ylethynyl)-6-methyl-pyridin-3-yl)amine hydrochloride

Following the same procedure as described in Example 1, (2-bromo-6-methyl-pyridin-3-yl)amine (150 mg, 0.80 mmol) reacted with (PPh$_3$)$_2$PdCl$_2$ (28 mg, 40 µmol), CuI (8 mg, 40 µmol) and 3-chloro-5-ethynyl-pyridine (165 mg, 1.20 mmol) in triethylamine (5 ml). The crude residue was purified by flash chromatography (hexane/ethyl acetate 7:3) to yield 141 mg (0.58 mmol, 72%) of (2-(5-chloro-pyridin-3-ylethynyl)-6-methyl-pyridin-3-yl)amine as a yellow solid.

The hydrochloride of (2-(5-chloro-pyridin-3-ylethynyl)-6-methyl-pyridin-3-yl)amine was prepared as described in Example 1 to yield 152 mg (0.48 mmol, 83%) of the title hydrochloride as a yellow solid.

R$_f$: 0.12 (Hexane/ethyl acetate 1:1). M. p.: 193° C. (dec.). $^1$H NMR (DMSO[D$_6$], 400 MHz) δ: 2.59 (s, 3 H), ), 5.81–7.41 (br. s, 2 H), 7.58 (d, J=8.8 Hz, 1 H), 7.73 (d, J=8.8 Hz, 1 H), 8.43–8.44 (m, 1 H), 8.79 (d, J=1.6 Hz, 1 H), 8.89 (d, J=2.0 Hz, 1 H). LC-MS (RT): 2.03 min.; MS (ES+) gave m/z: 244.0.

Example 11

(2-(3-Chloro-phenylethynyl)-6-methyl-pyridin-3-yl)amine hydrochloride

To a solution of CuI (5.0 mg, 28 µmol) in triethylamine (5 ml) were added (2-ethynyl-6-methyl-pyridin-3-yl)amine (75 mg, 0.57 mmol described in Example 7), (PPh$_3$)$_2$PdCl$_2$ (20 mg, 28 µmol), and 1-chloro-3-iodobenzene (135 mg, 0.57 mmol). The reaction mixture was stirred at room temperature for 4 h. The solvent was evaporated to afford a brown oil which was taken up in DCM and the solution was washed with water. The aqueous phase was extracted twice with DCM. The organic phases were dried over Na$_2$SO$_4$, filtered and concentrated. The crude residue was purified by flash chromatography (hexane/ethyl acetate 7:3) to yield 54 mg (0.22 mmol, 39%) of (2-(3-chloro-phenylethynyl)-6-methyl-pyridin-3-yl)amine as a yellow solid.

The hydrochloride of (2-(3-chloro-phenylethynyl)-6-methyl-pyridin-3-yl)amine was prepared as described in Example 1 to yield after trituration with diethyl ether 51 mg (0.16 mmol, 73%) of the title hydrochloride as a yellow powder.

R$_f$: 0.57 (hexane/ethyl acetate 1:1). M. p.: 195° C. (dec.). $^1$H NMR (DMSO[D$_6$], 400 MHz) δ: 2.51 (s, 3 H), 6.43–7.11 (br. s, 2 H), 7.50 (d, J=8.4 Hz, 1 H), 7.52-7.58 (m, 1 H), 7.59–7.69 (2 H), 7.72 (d, J=8.0 Hz, 1 H), 7.97 (s, 1 H). LC-MS (RT): 2.54 min.; MS (ES+) gave m/z: 243.0. Anal. Calcd for C$_{14}$H$_{12}$Cl$_2$N$_2$+0.5 H$_2$O: C, 58.35%; H, 4.55%; Cl, 24.61%; N, 9.72%. Found: C, 58.15%; H, 4.49%; Cl, 24.60%; N, 9.48%.

Example 12

(2-(3-Fluoro-phenylethynyl)-4.6-dimethyl-pyridin-3-yl)amine hydrochloride.

To a solution of 1.80 g (11.0 mmol) of 2-chloro-4,6-dimethyl-pyridin-3-ylamine (prepared as described in J. M. Klunder et al. J. Med. Chem., 35, 1992, 1887-1897) in toluene (10 ml) was added PBr$_3$ (18 ml). The reaction mixture was stirred for 48 h under reflux. After cooling the reaction mixture, it was poured onto ice, basified with NaOH 2 M solution (400 ml) and the aqueous phase was extracted twice with ethyl acetate. The combined organic phases were washed with brine, dried over Na$_2$SO$_4$, filtered and evaporated. The crude residue was purified by flash chromatography (cyclohexane/ethyl acetate 7:3) to yield 2.31 g (38%) of 2-bromo-4,6-dimethyl-pyridin-3-ylamine containing small amount of 2-chloro-4,6-dimethyl-pyridin-3-ylamine as a yellow oil.

To a solution of CuI (41 mg, 0.2 mmol) in triethylamine (12 ml) were added 2-bromo-4,6-dimethyl-pyridin-3-ylamine (870 mg, 4.33 mmol), (PPh$_3$)$_2$PdCl$_2$ (152 mg, 0.22 mmol), and 1-ethynyl-3-fluorobenzene (500 µl, 4.33 mmol). The reaction mixture was stirred for 30 min. at room temperature and for 3 h under reflux. The solvent was evaporated and the crude residue was purified by flash chromatography (cyclohexane/ethyl acetate 4:1) to yield 745 mg (3.10 mmol, 72%) of (2-(3-fluoro-phenylethynyl)-4,6-dimethyl-pyridin-3-yl)amine as a brown solid.

The hydrochloride of (2-(3-fluoro-phenylethynyl)-4,6-dimethyl-pyridin-3-yl)amine was prepared as described in Example 1 to yield after trituration with pentane 680 mg (2.46 mmol, 79%) of the title hydrochloride as a yellow powder.

R$_f$: 0.37 (cyclohexane/ethyl acetate 7:3). M. p.: 210° C. $^1$H NMR (DMSO[D$_6$], 500 MHz) δ: 2.33 (s, 3 H), 2.51 (s, 3 H), 6.31–6.72 (br. s, 3 H), 7.36–7.42 (m, 1 H), 7.47 (s, 1 H), 7.53–7.59 (m, 1 H), 7.60–7.63 (m, 1 H), 7.70–7.74 (m, 1 H). LC-MS (tr): 2.29 min.; MS (ES+) gave m/z: 241.1. Anal. Calcd for C$_{15}$H$_{14}$ClFN$_2$: C, 65.10%; H, 5.10%; Cl, 12.81%; F, 6.87%; N, 10.12%.

Found: C, 64.73%; H, 4.97%; Cl, 12.78%; F, 6.71%; N 9.87%.

Example 13

(2-(3-Chloro-phenylethynyl)-4.6-dimethyl-pyridin-3-yl)amine hydrochloride

To a solution of CuI (5.7 mg, 30 µmol) in triethylamine (1.6 ml) were added 2-bromo-4,6-dimethyl-pyridin-3-ylamine (120 mg, 0.60 mmol, described in Example 12), (PPh$_3$)$_2$PdCl$_2$ (21 mg, 30 µmol), and 1-ethynyl-3-chlorobenzene (98 mg, 0.72 mmol). The reaction mixture was stirred for 30 min. at room temperature and for 3 h under reflux. The solvent was evaporated and the crude residue was purified by flash chromatography (cyclohexane/ethyl acetate 4:1) to yield 39 mg (0.15 mmol, 25%) of (2-(3-chloro-phenylethynyl)-4,6-dimethyl-pyridin-3-yl)amine as a brown oil.

The hydrochloride of (2-(3-chloro-phenylethynyl)-4,6-dimethyl-pyridin-3-yl)amine was prepared as described in Example 1 to yield after trituration with pentane 25 mg (85 µmol, 57%) of the title hydrochloride as a yellow powder.

$R_f$: 0.37 (cyclohexane/ethyl acetate 7:3). M. p.: 204° C. LC-MS (tr): 2.56 min.; MS (ES+) gave m/z: 257.0.

Typical examples of recipes for the formulation of the invention are as follows:

1) Tablets

| | |
|---|---|
| Compound of the example 3 | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

In this example, the compound of the example 3 can be replaced by the same amount of any of the described examples 1 to 13.

2) Suspension:

An aqueous suspension is prepared for oral administration so that each 1 milliliter contains 1 to 5 mg of one of the described example, 50 mg of sodium carboxymethyl cellulose, 1 mg of sodium benzoate, 500 mg of sorbitol and water ad 1 ml.

3) Injectable

A parenteral composition is prepared by stirring 1.5% by weight of active ingredient of the invention in 10% by volume propylene glycol and water.

4) Ointment

| | |
|---|---|
| Compound of the example 3 | 5 to 1000 mg |
| Stearyl alcohol | 3 g |
| Lanoline | 5 g |
| White petroleum | 15 g |
| Water | ad 100 g |

In this example, the compound 3 can be replaced by the same amount of any of the described examples 1 to 13.

Reasonable variations are not to be regarded as a departure from the scope of the invention. It will be obvious that the thus described invention may be varied in many ways by those skilled in the art.

The invention claimed is:

1. A compound of formula

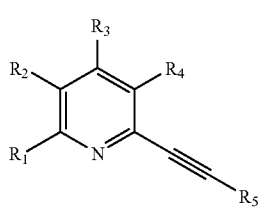

I but excluding 3-amino-4-chloro-6-methyl-2-(2-phenylethynyl)pyridine, wherein $R_1$ is methyl $R_2$ and $R_3$ are independently selected from hydrogen, halogen, nitro, $C_1$–$C_6$-alkyl;

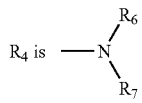

$R_6$ and $R_7$ which may be the same or different are hydrogen or a group of formula:

—X—$R_8$ wherein X is =CH—N($R_8$)$_2$ and $R_8$ is hydrogen, $C_1$–$C_6$-alkyl, halo-$C_1$–$C_6$-alkyl, aryl, aryl-$C_1$–$C_6$-alkyl, heteroaryl or heteroaryl-$C_1$–$C_6$-alkyl;

$R_5$ represents a group of formula

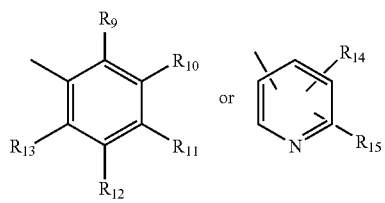

wherein $R_9$, $R_{10}$, $R_{11}$, $R_{12}$ and $R_{13}$ independently are hydrogen, halogen, cyano, nitro, $C_1$–$C_6$-alkyl, halo-$C_1$–$C_6$-alkyl, $C_1$–$C_8$-alkoxy, carboxy-$C_1$–$C_6$-alkyl or carboxyaryl;

$R_{14}$ and $R_{15}$ independently are as defined for $R_9$–$R_{13}$ above;

or a pharmaceutically acceptable salt of such compound of such compounds.

2. A compound according to claim 1 having the formula

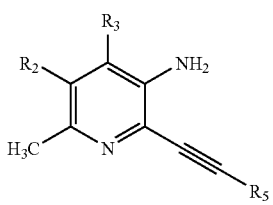

I-A wherein $R_2$ and $R_3$ are independently selected from hydrogen, $C_1$–$C_6$-alkyl;

$R_5$ represents a group of formula

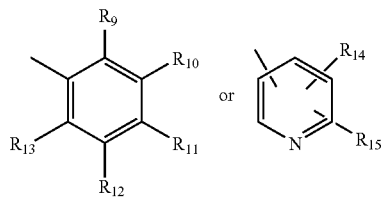

wherein $R_9$, $R_{10}$, $R_{11}$, $R_{12}$ and $R_{13}$ independently are hydrogen, halogen, cyano, nitro, $C_1$–$C_6$-alkyl, halo-$C_1$–$C_6$-alkyl, $C_1$–$C_6$-alkoxy, carboxy-$C_1$–$C_6$-alkyl or carboxyaryl;

$R_{14}$ and $R_{15}$ independently are as defined for $R_9$–$R_{13}$ above;

or a pharmaceutically acceptable salt of such compound of such compounds.

3. A compound according to claim 1 having the formula

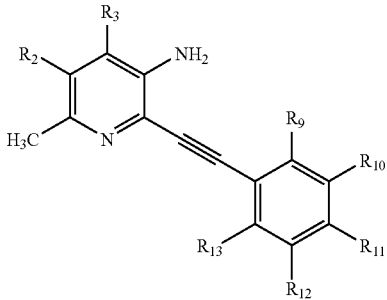

I-B wherein
- $R_2$ and $R_3$ are independently selected from hydrogen, $C_1$–$C_6$-alkyl;
- $R_9$, $R_{10}$, $R_{11}$, $R_{12}$ and $R_{13}$ independently are hydrogen, halogen, cyano, nitro, $C_1$–$C_6$-alkyl, halo-$C_1$–$C_6$-alkyl, $C_1$–$C_6$-alkoxy, carboxy-$C_1$–$C_6$-alkyl or carboxyaryl;
- or a pharmaceutically acceptable salt of such compound of such compounds.

4. A compound according to claim 1 having the formula

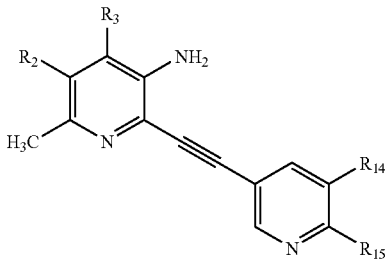

I-C wherein
- $R_2$ and $R_3$ are independently selected from hydrogen, $C_1$–$C_6$-alkyl;
- $R_{14}$ and $R_{15}$ independently are hydrogen, halogen, cyano, nitro, $C_1$–$C_6$-alkyl, halo-$C_1$–$C_6$-alkyl, $C_1$–$C_6$-alkoxy, carboxy-$C_1$–$C_6$-alkyl or carboxyaryl;
- or pharmaceutically acceptable salt of such compound of such compounds.

5. A compound according to claim 1, wherein said compound is selected from:
- (6-Methyl-2-phenylethynyl-pyridin-3-yl)amine,
- N,N-Dimethyl-N'-(6-methyl-2-phenylethynyl-pyridin-3-yl)-formamidine,
- (2-(3-Fluoro-phenylethynyl)-6-methyl-pyridin-3-yl)amine,
- (2-(3-Methoxy-phenylethynyl)-6-methyl-pyridin-3-yl)amine,
- (6-Methyl-2-pyridin-3-ylethynyl-pyridin-3-yl)amine,
- (2-(4-Fluoro-phenylethynyl)-6-methyl-pyridin-3-yl)amine,
- (2-(3,5-Difluoro-phenylethynyl)-6-methyl-pyridin-3-yl)amine,
- (2-(5-Fluoro-pyridin-3-ylethynyl)-6-methyl-pyridin-3-yl)amine,
- (3-(3-Amino-6-methyl-pyridin-2-ylethynyl)-benzonitrile,
- (2-(5-Chloro-pyridin-3-ylethynyl)-6-methyl-pyridin-3-yl)amine,
- (2-(3-Fluoro-phenylethynyl)-4,6-dimethyl-pyridin-3-yl)amine,
- (2-(3-Chloro-phenylethynyl)-4,6-dimethyl-pyridin-3-yl)amine, or a pharmaceutically acceptable salt thereof.

* * * * *